(12) United States Patent
Kolte et al.

(10) Patent No.: US 7,091,394 B2
(45) Date of Patent: Aug. 15, 2006

(54) DRESSING

(75) Inventors: Mette Irene Kolte, Soeborg (DK); Anne Mette Wolsing, Fredensborg (DK); Jeppe Stigsen, Birkerod (DK); Jette Kvisgaard, Hoersholm (DK)

(73) Assignee: Coloplast A/S, Humlebaek (DK)

(*) Notice: Subject to any disclaimer, the term of this patent is extended or adjusted under 35 U.S.C. 154(b) by 188 days.

(21) Appl. No.: 10/416,503

(22) PCT Filed: Nov. 9, 2001

(86) PCT No.: PCT/DK01/00741

§ 371 (c)(1),
(2), (4) Date: Oct. 22, 2003

(87) PCT Pub. No.: WO02/39940

PCT Pub. Date: May 23, 2002

(65) Prior Publication Data

US 2004/0049146 A1    Mar. 11, 2004

(30) Foreign Application Priority Data

Nov. 20, 2000 (DK) .............................. 2000 01745

(51) Int. Cl.
*A61F 13/00* (2006.01)

(52) U.S. Cl. ........................................... 602/42
(58) Field of Classification Search ............ 602/41–59; 424/443–449; D24/189; 128/888, 889; 604/304–306
See application file for complete search history.

(56) References Cited

U.S. PATENT DOCUMENTS

| 1,691,440 | A | | 11/1928 | Hodgson |
| 2,253,108 | A | | 8/1941 | Casey .......................... 128/157 |
| 2,440,235 | A | | 4/1948 | Solomon ..................... 128/157 |
| 3,900,027 | A | * | 8/1975 | Keedwell ..................... 604/307 |
| 4,367,732 | A | | 1/1983 | Poulsen et al. ............. 128/156 |
| 5,820,578 | A | | 10/1998 | Johansen ...................... 602/57 |
| 5,827,213 | A | | 10/1998 | Jensen ......................... 602/62 |

FOREIGN PATENT DOCUMENTS

| CH | 321693 | 6/1957 |
| EP | 0 552 271 | 4/1996 |
| EP | 1 008 330 | 6/2000 |
| FR | 2793406 | 11/2000 |
| JP | 2000024026 | 1/2000 |
| JP | 2000109427 | 4/2000 |
| JP | 2000209429 | 7/2000 |
| WO | 89/05619 | 6/1989 |
| WO | 92/05756 | 4/1992 |
| WO | 94/15562 | 7/1994 |

\* cited by examiner

*Primary Examiner*—Henry Bennett
*Assistant Examiner*—Dinnatia Doster-Greene
(74) *Attorney, Agent, or Firm*—Jacobson Holman PLLC

(57) ABSTRACT

A wound dressing for application to a protruding part of a joint of the body, in particular the heel. The dressing includes an elongated first part for placing on one side of the protruding joint part, and a second part for placing on another side of the joint, and two ear parts extending laterally from the second part. At least the central parts of the first part, the second part and the ear parts of the dressing are covered with an absorbent element. A portion of each laterally extending ear part between its outermost lateral point and a longitudinal tip of the second part is concave to facilitate wrapping of the ear parts around the heel without overlapping of the absorbent element.

20 Claims, 3 Drawing Sheets

DRESSING

FIELD OF THE INVENTION

The present invention relates to a dressing, especially a wound dressing. The wound dressing is especially suitable for use in treatment of wounds located on protruding parts of a joint of the body such as the heel or elbow.

BACKGROUND OF THE INVENTION

Wounds on protruding parts of the body are due to the anatomical complexity of the area very difficult to secure a dressing or bandage to. Efforts have been made to achieve better conformity, often by providing such dressings with irregular outlines.

To ensure good quality of life for a patient with a heel wound it is important that the dressing is pleasant to wear and also can be used when the patient is active, e.g. walking, and together with shoes. This requires a dressing being flexible, pliable and safely secured to the foot. Too bulky dressings or dressings with folds, flaps or sharp edges may give rise to discomfort or pressure points leading to pressure sores which are highly undesired. Furthermore, it is desirable if the dressing is capable of fitting a variety of shapes and sizes of the body parts and wounds without the necessarity of adaptation of the dressing e.g. by cutting.

Every time a wound dressing is changed, both the wound and the skin surrounding the wound is exposed to severe stress. It is therefore desired that the dressing is allowed to stay on the patient for as long as possible. This requires a dressing with good absorbency and an excellent fit to the anatomy of the body part.

The dressings may often comprise hydrocolloid as absorbent material, which has a limited absorption. When used on medium or highly exuding wounds, this leads to a more frequent change of dressing as well as the risk of maceration, leakage, detachment and contamination of the wound is increased.

In U.S. Pat. No. 5,827,213 (Jensen) is disclosed a planar dressing comprising an absorbent adhesive, such as hydrocolloid. The dressing comprises a central portion and a border portion surrounding the central portion. The border portion is having a thickness substantially less than the central portion. The dressing comprises at least one triangular gusset part extending from the border portion of the dressing and into the central portion. The gusset comprises an inwardly-extending fold line by use of which the dressing may be folded to a three-dimensional structure before application to the heel. It is only possible to apply the dressing in one way, and the folded gussets may give rise to uncomfort by sticking to the clothes or to pressure sores.

Heel ulcers are usually located on the plantar or on the side or dorsum of the foot. A wound dressing being flexible enough to cover different parts or all the mentioned parts of the foot may be preferred.

Various dressings for protruding body parts are known:

U.S. Pat. No. 2,440,235 (Solomon) discloses a T-shaped finger dressing. The stem of the T is covered by a substantially rectangular absorbent pad.

U.S. Pat. No. 2,253,108 (Casey) discloses a finger dressing with a central absorbent pad. The dressing is slitted in the length direction in order to achieve folding around the finger tip.

In CH Patent No. 321 693 (Conrads) is disclosed a wound dressing for the finger tip. The dressing comprises a first and a second part with an elongated absorbent pad extending from the first to the second part. An adhesive flange is extending from the absorbent pad of the second part. Incisions between the first and the second part renders it possible to avoid bulks when the dressing is folded around a finger tip.

However the structure of the three above mentioned dressings, when applied to the finger tip, is essentially two-dimensional and will not be suitable for application to a joint, such as the heel or the elbow.

European Patent No. 552 271 (Smith & Nephew) discloses a three-dimensional wound dressing of an absorbent material such as foam. The dressing is welded together to develop the form of an envelope to enclose the heel. It is not possible to adjust the size of the dressing to the heel resulting in discomfort. Thus it will only fit a limited range of sizes of body parts and a secondary dressing may further be needed to secure the dressing to the patient. The welded line may give rise to pressure sores as well as the absorption at this line may be limited.

U.S. Pat. No. 5,820,578 (Johansen) discloses a wound dressing comprising a central part and a plurality of adhesive flaps extending radially from the central part. The flaps are capable of moving and bending independently of each others. The dressing is most suitable for minor wounds, as it will be bulky if enlarged. Further, the adhesive may cold-flow and hereby connect the adhesive flaps in an undesired manner.

Thus, there is still a need for a conformable dressing with high absorbency, and an ability to fit different wound sites on protruding parts of a joint of the body, without wrinkling or appearing bulky. It has surprisingly been found that it is possible to achieve such a dressing by a dressing according to the present invention.

BRIEF DESCRIPTION OF THE INVENTION

The invention relates to a wound dressing for application to a protruding part of the body which dressing comprises an elongated first part for placing on one side of the protruding part of the body, and a second part for placing on another side of the body, and two ear parts extending from the second part.

BRIEF DESCRIPTION OF THE DRAWINGS

The invention is explained more in detail with reference to the drawings in which.

DETAILED DESCRIPTION OF THE INVENTION

Figure 1:
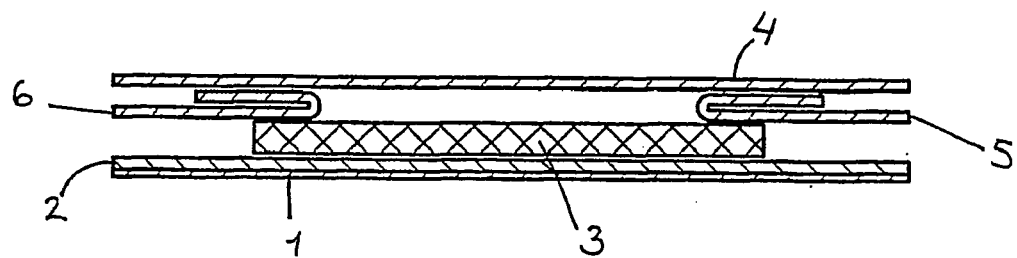
FIG. 1 shows a cross-section of an embodiment of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention relates to a wound dressing for application to a protruding part of a joint of the body which dressing comprises an elongated first part for placing on one side of the protruding part of the joint, and a second part for placing on another side of the joint, and two ear parts extending from the second part, wherein at least the central parts of the first, the second part and the ear parts of the dressing are covered with an absorbent element, wherein at least a part of said absorbent element extends to the edge of at least one of the parts of the dressing, and wherein the side edges of the absorbent element of the first part are essentially in an angle of 45–120 degrees to the neighbouring edges of the absorbent element of the ear parts.

The side edges of the absorbent element of the first part may preferably be in essentially an angle of 60–110 degrees to the neighbouring edges of the absorbent element of the ear parts.

More preferred, side edges of the absorbent element of the first part may be in essentially an angle of 75–100 degrees to the neighbouring edges of the absorbent element of the ear parts.

Most preferred, the side edges of the absorbent element of the first part may be essentially perpendicular to the neighbouring edges of the absorbent element of the ear parts.

By having an angle of less than 180 degrees between the two side edges of the absorbent element, a three-dimensional structure of the absorbent element is achieved when the dressing is applied to a body part.

The joint which is to be covered by the dressing according to the invention will often but not always be substantially rectangular. By adapting the angle between the two neighbouring side edges of the absorbent element to the angle of body part a perfect fit of the dressing is achieved. An angle of less than 90 degrees in the dressing will fit a joint of more than 90 degrees, and an angle of more than 90 degrees of the dressing will fit joints of less than 90 degrees.

In one embodiment of the invention the absorbent element extends to the side edges of the first part and the remaining edges are provided with an adhesive flange.

In another embodiment of the invention the absorbent element extends to the side edges of at least a part of the ear parts and the remaining edges are provided with an adhesive flange.

The absorbent element extends to at least some of the ear parts of the dressing. Preferably the extension of the absorbent element is substantially perpendicular to the first elongated part of the dressing. This renders it possible to abut the edges of the absorbent element forming a three-dimensional dressing adapted to the part of the body essentially without a discontinuous seam area.

By extending a part of the absorbent element to the edge of the dressing several advantages are achieved. When there is no adhesive flange along a part of the absorbent element, the absorbent element of the dressing may, when applied to a protruding body part, create a large continuous area of absorbent material as the perpendicular edges will abut or overlap into a three-dimensional wound contacting part. The overlap may render it possible to fit the dressing to different sizes of body parts e.g. heels, without having to adapt the size of the dressing, e.g. by cutting, or use different sizes of dressings. When using a soft and pliant absorbent element, e.g. a foam, the overlap will not give rise to bulkiness or pressure points.

When applied to a protruding body part such as the heel, the part of the dressing comprising the absorbent element extending to the edge of the dressing is first applied and fixed, and then the rest of the dressing is folded around the heel enclosing the wound. The ear parts will ensure a smooth surface with no flaps or folds capable of giving rise to pressure points.

The skin-facing parts of the dressing may be partly or fully covered with adhesive.

The dressing is planar until application, and will during application enter a three-dimensional structure rendering it possible to adapt to a large variety of shapes and sizes of the body part and of the wound.

By having substantially concave outlines of the dressing of the invention a high flexibility of the dressing is achieved.

The flexibility of the dressing may be further enhanced by notches or slits in the edge portion of the dressing according to the invention.

The large flexibility of the dressing renders it possible to apply the dressing in different positions of the body part. When treating heel wounds, some of these are located on the side of the heel. This makes it difficult to use traditional heel dressings as these are designed to be applied symmetrically around the heel. The dressing according to the invention, however, may be applied on the side of the heel without problems, due to the high flexibility of the dressing.

By having an absorbent element, a good absorption capacity is achieved. The continuous three-dimensional absorbent element developed during application secures a full cover of the wound site, diminishing the risk of leakage and contamination.

A broad adhesive flange around the dressing secures the dressing to the body part and prolongs wear-time. Further, the flange smoothens the edges of the dressing, diminishing the risk of pressure points and making it easier for the patient to put on socks and shoes. If the edges of the dressing is extended in the direction of the Achilles the dressing will have a lower risk of interference with the shoes when having the dressing on a heel wound.

The absorbent element may be adherent or comprise adhesive.

It may be desirable if the absorbent element is not adhesive, as the shearing forces then will be distributed over a large area and thus reduce the stress to the skin. The adhesive flange around the absorbent element is preferably relatively broad, as this will provide good adherence of the dressing even under heavy stress, as well as it renders it possible to make adjustments by cutting the dressing to fit individual needs without interfering with the absorbent element.

The absorbing element may be a natural or synthetic material such as CMC alginate or other polysaccharides, non-woven layer or foam. The absorbent pad may also include any superabsorbing material.

In one embodiment of the invention the absorbent element is a foam.

In a preferred embodiment the foam is a polyurethane.

The absorbent element may have different sizes or shapes, depending on the wound and/or body part to be applied to. In one embodiment of the invention the absorbent element extends from the first elongated part of the dressing and over the second part of the dressing.

In another embodiment of the invention the absorbent pad further extends over the ear parts of the dressing, creating a pair of "wings", the edges of these wings being substantially perpendicular to the first elongated part. When the dressing is assembled on the body part the two perpendicular edges of the absorbent element will abut due to the lack of adhesive flange on one of the edges, and creating a continuous absorbent wound element. The adhesive flanges of the ear part will ensure no leakage.

The absorbent element may comprise slits or indentations in order to enhance the flexibility of the dressing.

The adhesive flange at the end of the elongated first part may be broader than the part being covered by the absorbent element.

The absorbent element is preferably a relatively thick foam pad, rendering it possible to obtain cushioning through pressure redistribution over the wound together with a superior exudate handling, diminishing leakage and maceration.

The dressing may include a top layer, such as a film, a non-woven layer or a foam. The top layer is preferably flexible and conformable top layer and an adhesive layer covering at least the edge portion of the skin contacting surface of the top layer. An absorbent element may be located at the central part of the coated top layer leaving parts of the adhesive coated top layer as a discontinuous flange surrounding the absorbent element.

The top layer of the dressing according to the invention may be any layer, such as a polyurethane film, foam or non-woven layer or combination of films or layers which, in combination with the adhesive, shows the desired characteristics of the dressing according to the invention. The film may e.g. be produced from a polyolefinic material, polyurethane material or polyethylene.

The top layer is preferably permeable to vapour but impermeable to water.

A preferred material for the top layer may be polyurethane.

The top layer is partly or fully covered with an adhesive. The coating may be in the form of a pattern or e.g. only situated on the flange.

The adhesive of a dressing of the invention may be any skin-friendly adhesive known per se being able to adhere to the skin, the mucosa and/or a wound on any portion of a living being and is preferably an adhesive comprising a hydrocolloid. A suitable adhesive is e.g. a hydrocolloid-containing moisture absorbing material such as the adhesive disclosed in U.S. Pat. No. 4,367,732. The adhesive may also comprise a skin friendly acrylate adhesive containing hydrophilic areas. The adhesive may be essentially uniform or be constituted by distinct areas having different composition such as the adhesives disclosed in WO89/05619 or in WO94/15562.

Suitable hydrocolloids for incorporation in the adhesive compositions of the invention are selected from naturally occurring hydrocolloids, semi-synthetic hydrocolloids and synthetic hydrocolloids.

More particularly, the hydrocolloids are preferably selected from guar gum, locust bean gum (LBG), pectin, alginates, gelatine, xanthan and/or gum karaya; cellulose derivatives (e.g. salts of carboxymethylcellulose such as sodium carboxymethylcellulose, methylcellulose and hydroxypropylmethylcellulose) and/or sodium starch glycolate and/or polyvinylalcohol and/or polyethylene glycol.

In a preferred embodiment of the invention the adhesive includes hydrocolloid. A thin and flexible hydrocolloide is preferred, rendering it possible to obtain maximum flexibility and stretchability of the dressing, and thereby prolonging the wear time of the dressing.

A dressing according to the invention is typically in the form of a laminate comprising a top layer, a layer of adhesive, an absorbent element, and is optionally covered in part or fully by one or more release liners or cover films to be removed before use. The dressing may further comprise a top layer to be removed before use.

The skin-contacting surface of the dressing may be covered by one or more release liners.

Release liners which are especially suitable for use with the dressing of the invention can be made of kraft papers, polyethylene, polypropylene, polyester or composites of any of these materials. The liners are preferably coated with release agents such as fluorochemicals or silicones. The release liner may, if present, be removed before, during, or after application. If only removed after application, the release liner may act as a tab member or handle during application.

The construction of the release liner may ease the application of the dressing to a body part. In a preferred embodiment of the invention the release liner is divided into three parts: A central part covering the elongated first part and the second part, and two tab members on the ear parts of the dressing. These tab members renders it possible to handle the dressing during the application to the patient more easily. Application is as follows: First, the central part of the release liner is removed, then the dressing is folded to an approximately 90° angle at the transition between first elongated part and the second part to exactly fit the shape of the heel. The adhesive flange at the end of the first elongated part is secured to the skin above the heel, along the Achilles, so that the folding line corresponds to the edge of the heel. The rest of the disclosed adhesive is secured under the foot. One of the tab members is removed and that ear part of the dressing is applied in a way that the edges of the foam either abut or overlap. The same is done for the remaining ear part while assuring that the dressing is applied so that it conforms to the shape of the foot.

A three-part system of one release-liner and two tab members on the ear parts of the dressing is easy to use and ensures that the dressing is aseptically applied and positioned correct the first time.

The release liner is not present during the use of the dressing of the invention and is therefore not an essential part of the invention itself.

The dressing may further comprise one or more pharmaceutically active ingredients.

The dressing according to the invention may comprise wound healing associated indicator(s) such as indicators of pH, partial pressure of O2, temperature, radical mechanisms or biotechnological assays, e.g. indicating formation of collagen.

It is also advantageous that a dressing according to the invention comprises wound healing associated indicator(s), cushions or similar device for treatment or prophylaxis of formation of wounds and/or skin abnormalities.

This opens for a combined medical treatment of the wound and an easy and sterile application of the active ingredients, e.g. by incorporating active ingredients such as a cytochine such as growth hormone or a polypeptide growth factor giving rise to the incorporation of such active substances in a form being apt to local application in a wound in which the medicament may exercise its effect on the wound, other medicaments such as bacteriostatic or bactericidal compounds, e.g. iodine, iodopovidone complexes, chloramine, chlorohexidine, silver salts such as sulphadiazine, silver nitrate, silver acetate, silver lactate, silver sulphate, silver-sodium-thiosulphate or silver chloride, zinc or salts thereof, metronidazol, sulpha drugs, and penicillins, tissue-healing enhancing agents, e.g. RGD tripeptides and the like, proteins, amino acids such as taurine, vitamins such as ascorbic acid, enzymes for cleansing of wounds, e.g. pepsin, trypsin and the like, proteinase inhibitors or metalloproteinase inhibitors such as Illostat or ethylene diamine tetraacetic acid, cytotoxic agents and proliferation inhibitors for use in for example surgical insertion of the product in cancer tissue and/or other therapeutic agents which optionally may be used for topical application, pain relieving agents such as lidocaine or chinchocaine, emollients, retinoids or agents having a cooling effect which is also considered an aspect of the invention.

The dressing according to the present invention is suitable for application on protruding parts of the body, such as heel or elbow, finger or toe. The dressing is especially suitable for application to the heel.

DETAILED DESCRIPTION OF THE DRAWING

In FIG. 1 is shown an embodiment of the invention in cross-section. The dressing includes a top layer (1), covered with an adhesive layer (2) and an absorbent element (3). The skin-contacting surface of the dressing may optionally be covered by one or more release liners, three (4, 5, 6) in the embodiment shown, the two folded release liners (5, 6) serving as tab members or handles during the application of the dressing.

Figure 2:
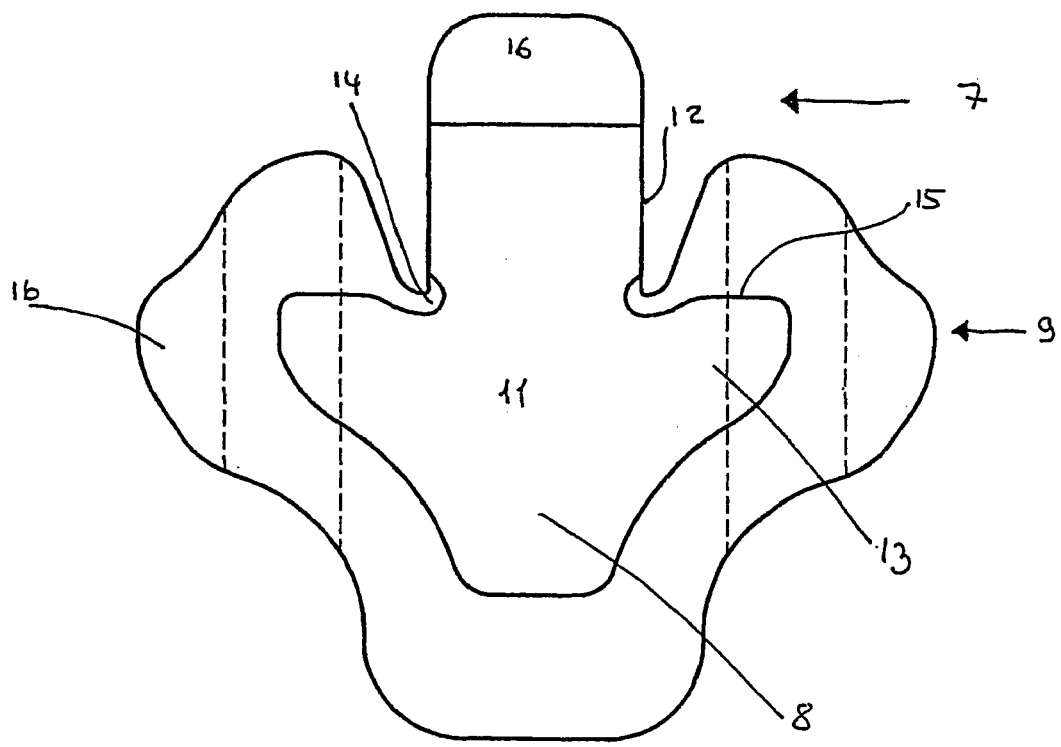
FIG. 2 shows a an embodiment seen from below.

FIG. 2 shows the same embodiment of the invention seen from below. The dressing includes a first elongated part (7) and a second part (8), from which two ear parts (9) are laterally extending. As shown, a part of the laterally extending ear parts also extends longitudinally so as to extend in the same direction as the elongated first part, and a portion of each ear part between an outermost lateral point and the tip of the free end of the second part is concave. The dressing further includes an absorbent element (11) which is extending to the edge of the dressing (12) at a part of the first elongated part. The absorbent element (11) extends to the ear parts (13) extending from the second part of the dressing (8). In the angle between the elongated first part (7) and the second part (8), the absorbent element may have an incision (14) in order to smooth the corner of the dressing when applied. The concave portion also facilitates wrapping of the ear parts around the heel in a non-overlapping manner with respect to the absorbent element. The side edges (12) of the absorbent element of the first part are essentially perpendicular to the neighbouring edges of the absorbent element of the ear parts (15). The ear parts and the elongated first part are provided with a broad, adhesive flange (16). The position of the release-liners are shown as dotted lines.

Figure 3:
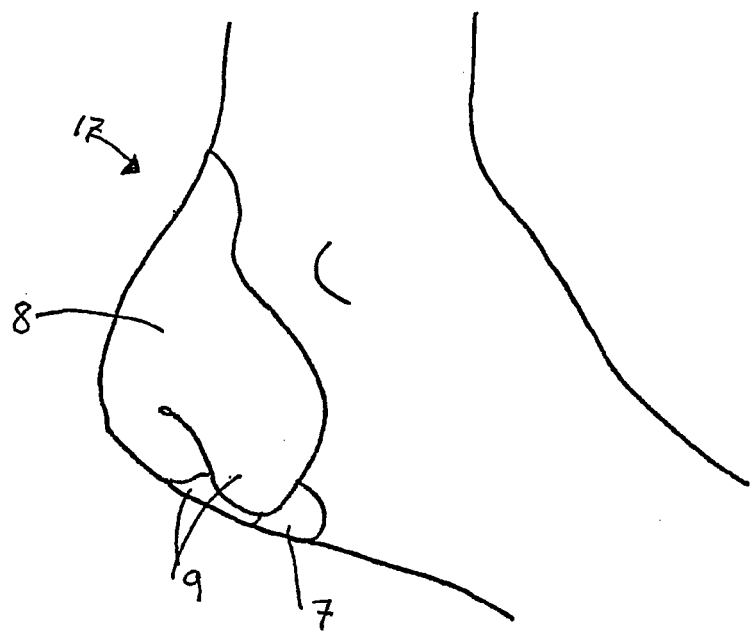
FIG. 3 shows a dressing of the invention, applied to a heel.

FIG. 3 is showing the same embodiment of the invention applied to the heel (17). The elongated first part (7) of the dressing is secured under the heel, the second part (8) up along the Achilles, end the ear parts (9) are secured under the foot, on top of the elongated first part.

Figure 4:
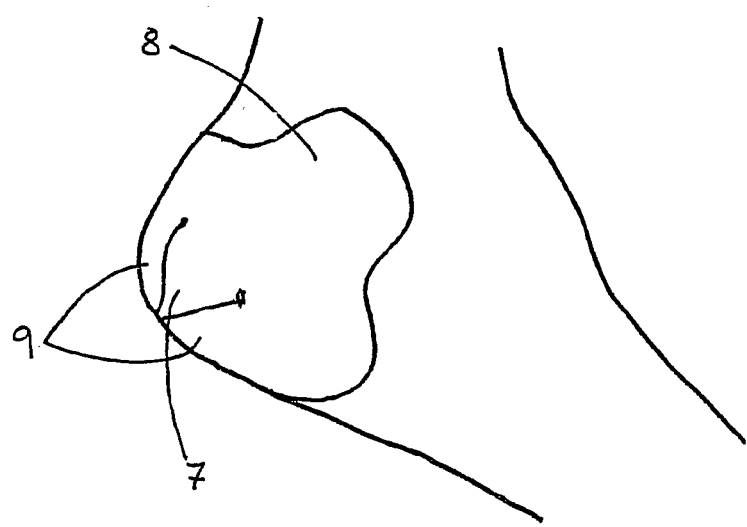
FIG. 4 shows a dressing of the invention applied to the side of a heel.

The dressing may also be applied to the side of the heel as shown in FIG. 4. In this case the elongated first part (7) of the dressing is secured along the edge of the heel, and the second part (8) of the dressing is secured to the side of the foot. The ear parts (9) are secured around the sides of the heel.

Figure 5:
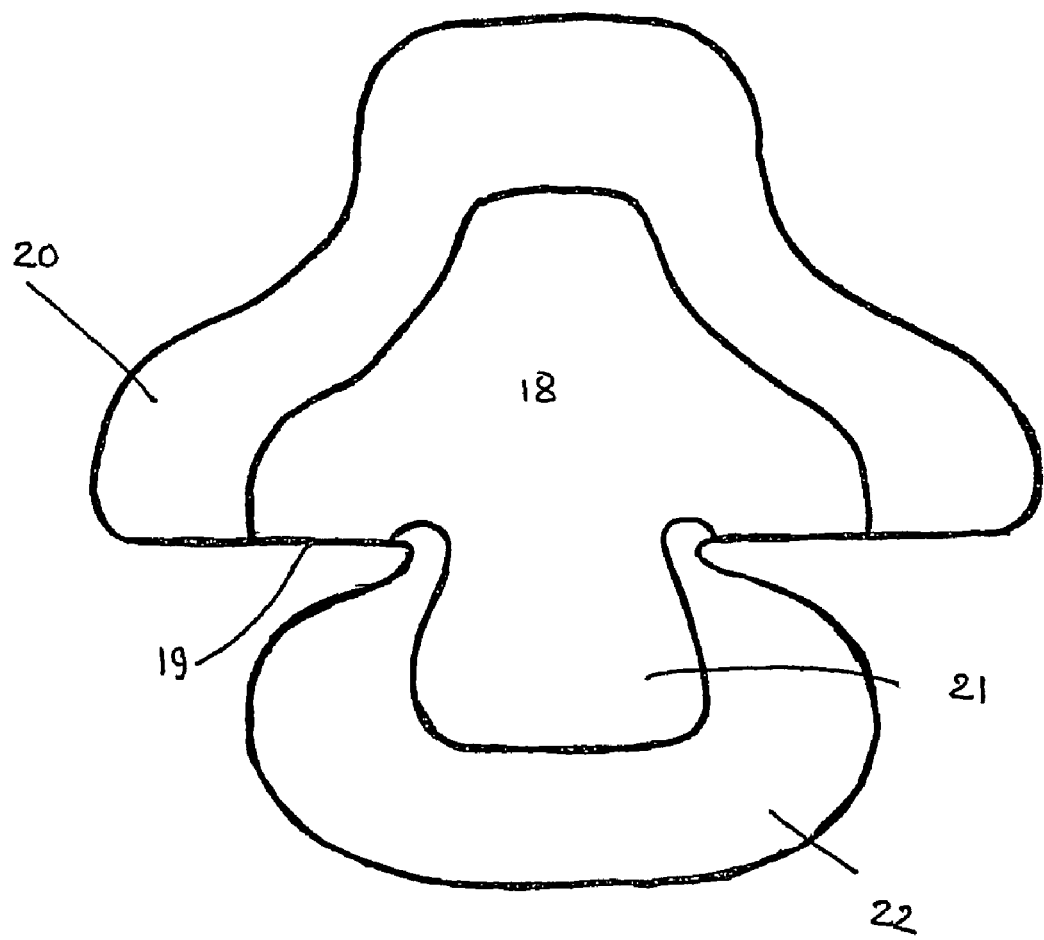
FIG. 5 shows another embodiment of the invention.

FIG. 5 shows another embodiment of the invention. In this embodiment the absorbent element (18) is extending to the edge (19) of the ear parts (20), while the absorbent element of the first elongated part (21) is surrounded by an adhesive flange (22). In this embodiment two release-liners will be appropriate, one covering the elongated first part and a second covering the rest of the dressing. When applied, the second part of the dressing and the ear parts are secured first, and the wound is then enclosed by the first elongated part.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A wound dressing for application to a person's heel comprising an elongated first part having a free end for placing on one side of the heel, a second part extending in longitudinal alignment with said first part for placing on another side of the heel, said second part having a free end opposite said first part free end, and two ear parts extending laterally from each side of the second part to define outermost lateral points on each side of said dressing, at least central parts of the first part, the second part and the ear parts of the dressing being covered with an absorbent element, a part of each laterally extending ear part also extending longitudinally so as to extend in a same direction as the free end of said first part, a portion of each of said ear parts between said second part free end and each of said outermost lateral points being concave to facilitate wrapping of said ear parts around the heel in a non-overlapping manner with respect to said absorbent element.

2. The dressing as set forth in claim 1, wherein said longitudinally extending part of each ear part is adjacent and spaced from a respective side edge of said first part.

3. The dressing as set forth in claim 2, wherein said longitudinally extending part of said ear parts defines an acute angle with said respective side edges of said first part.

4. The dressing as set forth in claim 1, wherein at least a part of said absorbent element extends to the edge of at least one of the parts of the dressing.

5. The dressing as set forth in claim 4, wherein the side edges of the absorbent element of the first part are essentially in an angle of 45–120 degrees to the neighbouring edges of the absorbent element of the ear parts.

6. The dressing as set forth in claim 1, wherein a portion of each of said ear parts between an outermost longitudinal point furthest from said second part free end and the outermost lateral point is concave to facilitate wrapping of said ear parts around the heel.

7. The dressing as set forth in claim 3, wherein the absorbent element has an incision adjacent a vertex of said acute angle to facilitate wrapping of said ear parts around the heel in a non-overlapping manner with respect to said absorbent element.

8. The dressing as set forth in claim 1, wherein the absorbent element extends to the side edges of the first part and the remaining edges are provided with an adhesive flange.

9. The dressing as set forth in claim 1, wherein the absorbent element extends to the side edges of at least a part of the ear parts and the remaining edges are provided with an adhesive flange.

10. The dressing as set forth in claim 1, wherein side edges of the absorbent element of the first part are essentially in an angle of 60–110 degrees to neighbouring edges of the absorbent element of the ear parts.

11. The dressing as set forth in claim 1, wherein side edges of the absorbent element of the first part are essentially in an angle of 75–100 degrees to neighbouring edges of the absorbent element of the ear parts.

12. The dressing as set forth in claim 1, wherein side edges of the absorbent element of the first part are essentially perpendicular to neighbouring edges of the absorbent element of the ear parts.

13. The dressing as set forth in claim 1, wherein the skin-facing parts of the dressing are partly or fully covered with adhesive.

14. The dressing as set forth in claim 1, wherein the absorbent element is a foam.

15. The dressing as set forth in claim 1, wherein the absorbent element includes slits or indentations.

16. The dressing as set forth in claim 1, wherein the edge portion of the dressing includes notches or slits.

17. The dressing as set forth in claim 1, wherein the dressing includes one or more pharmaceutically active ingredients.

18. A method of applying a wound dressing to a person's heel, the dressing having an elongated first part with a free end for placing on one side of the heel, a second part extending in longitudinal alignment with said first part for placing on another side of the heel, said second part having a free end opposite said first part free end, and two ear parts extending laterally from each side of the second part to define outermost lateral points on each side of said dressing, at least central parts of the first part, the second part and the ear parts of the dressing being covered with an absorbent element, a part of each laterally extending ear part also extending longitudinally so as to extend in a same direction as the free end of said first part, and a portion of each of said ear parts between said second part free end and each of said outermost lateral points being concave, said method comprising the steps of:

a) securing the elongated first part to a first part of the heel;

b) securing the second part to a second part of the heel; and c) securing the ear parts so that said central parts covered with said absorbent element are in a non-overlapping relationship.

19. The method as set forth in claim 18, wherein step a) includes securing the elongated first part under the heel, step b) includes securing the second part to the back of the heel over the Achilles tendon thereof, and step c) includes securing the ear parts under the foot.

20. The method as set forth in claim 18, wherein step a) includes securing the elongated first part under an edge of said heel, step b) includes securing the second part to a side of the heel and an adjacent side of the foot, and step c) include securing the ear parts around the sides of the heel.

* * * * *